US007674271B2

(12) United States Patent  
Bjerken

(10) Patent No.: US 7,674,271 B2
(45) Date of Patent: Mar. 9, 2010

(54) ENDOLUMINAL GASTRIC RING AND METHOD

(75) Inventor: David Bjerken, Marietta, GA (US)

(73) Assignee: InTailor Surgical, Inc., Marietta, GA (US)

( * ) Notice: Subject to any disclaimer, the term of this patent is extended or adjusted under 35 U.S.C. 154(b) by 494 days.

(21) Appl. No.: 11/327,348

(22) Filed: Jan. 9, 2006

(65) Prior Publication Data

US 2006/0253142 A1 Nov. 9, 2006

Related U.S. Application Data

(63) Continuation-in-part of application No. 11/267,321, filed on Nov. 7, 2005, and a continuation-in-part of application No. 11/267,266, filed on Nov. 7, 2005, now abandoned.

(60) Provisional application No. 60/748,148, filed on Dec. 8, 2005, provisional application No. 60/698,941, filed on Jul. 14, 2005, provisional application No. 60/697,544, filed on Jul. 11, 2005, provisional application No. 60/677,355, filed on May 4, 2005, provisional application No. 60/677,345, filed on May 4, 2005.

(51) Int. Cl.
*A61B 17/04* (2006.01)

(52) U.S. Cl. ...................................... 606/144; 606/153

(58) Field of Classification Search ............... 623/23.65, 623/2.11; 604/264; 606/139, 144, 146, 148, 606/153, 157

See application file for complete search history.

(56) References Cited

U.S. PATENT DOCUMENTS 4,957,499 A * 9/1990 Lipatov et al. ............... 606/153
5,330,503 A 7/1994 Yoon
5,792,152 A 8/1998 Klein et al.
6,048,351 A * 4/2000 Gordon et al. ............... 606/144
6,464,701 B1 10/2002 Hooven et al.

(Continued)

*Primary Examiner*—(Jackie) Tan-Uyen T Ho
*Assistant Examiner*—Mark Mashack

(57) ABSTRACT

A ring or rings adapted for endoluminal placement within the stomach, other hollow organ or vessel, and a method for deploying the rings is described. The rings create a small pouch with a reinforced stoma in the stomach for the treatment and control of obesity. An endoluminal suturing device for deploying a circumferential line of interrupted mattress suture bites is inserted into the patient's stomach via the patient's mouth. The distal gastric ring is preloaded on the distal end of the suturing device and is incorporated with suture loops from the double-armed sutures contained within the device. The suturing device can have an expandable area at its distal end that can expand its diameter to between approximately 10 mm and 150 mm. The circumference of this expanded area has a suction opening that is used to draw in tissue when a vacuum is applied to the device. Flexible cannulas containing long flexible suture needles are positioned radially around the circumference of the suction opening. The long needles are adapted to be advanced through the drawn in tissue incorporating their attached suture material. The expandable area of the device is collapsed, and the device is withdrawn from the patient. With the distal ring anchoring the sutures beneath the incorporated tissue folds, a column of sutures exits the device's suction port as the device is withdrawn. A second, proximal ring is then incorporated with the sutures and may then be endoscopically lowered into the patient's stomach and positioned proximal to the distal ring. The sutures are endoscopically secured and cut, thereby fixing the two rings together with tissue incorporated between them.

67 Claims, 15 Drawing Sheets

U.S. PATENT DOCUMENTS

| | | | |
|---|---|---|---|
| 6,464,707 B1 * | 10/2002 | Bjerken | 606/139 |
| 6,558,400 B2 | 5/2003 | Deem et al. | |
| 6,572,629 B2 | 6/2003 | Kalloo et al. | |
| 6,675,809 B2 | 1/2004 | Stack et al. | |
| 6,769,590 B2 * | 8/2004 | Vresh et al. | 227/19 |
| 6,773,440 B2 | 8/2004 | Gannoe et al. | |
| 6,845,776 B2 | 1/2005 | Stack et al. | |
| 6,997,931 B2 | 2/2006 | Sauer et al. | |
| 7,111,627 B2 | 9/2006 | Stack et al. | |
| 7,121,283 B2 | 10/2006 | Stack et al. | |
| 7,141,055 B2 * | 11/2006 | Abrams et al. | 606/115 |
| 7,152,607 B2 | 12/2006 | Stack et al. | |
| 2002/0072761 A1 * | 6/2002 | Abrams et al. | 606/190 |
| 2004/0082963 A1 * | 4/2004 | Gannoe et al. | 606/153 |
| 2004/0181238 A1 * | 9/2004 | Zarbatany et al. | 606/108 |
| 2005/0038468 A1 * | 2/2005 | Panetta et al. | 606/200 |

* cited by examiner

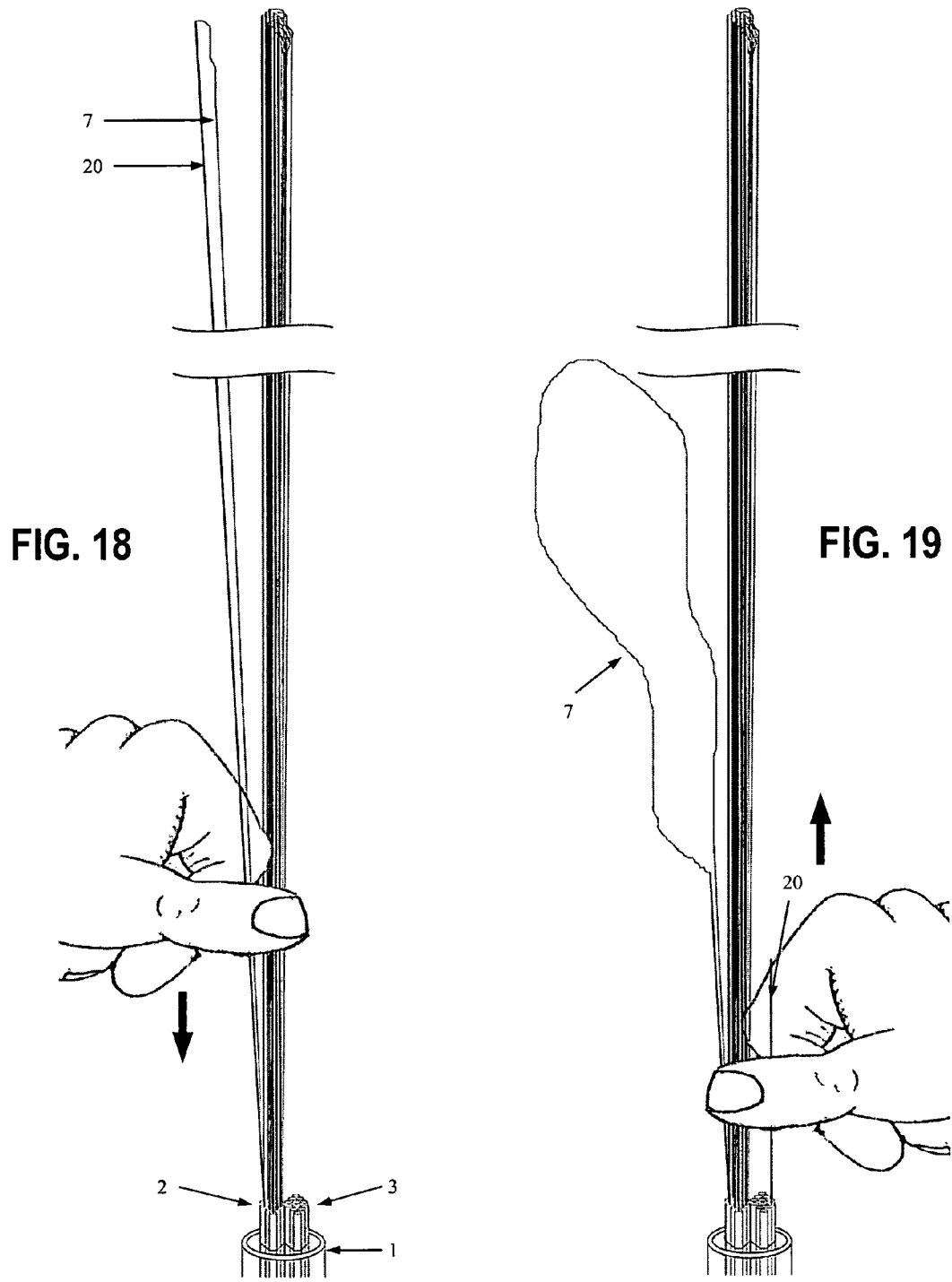

ENDOLUMINAL GASTRIC RING AND METHOD

CROSS-REFERENCE TO RELATED APPLICATIONS

This application claims priority to Provisional Patent Application No. 60,677,345, filed May 4, 2005; Provisional Patent Application No. 60/677,355, filed May 4, 2005; Provisional Patent Application No. 60/697,544, filed Jul. 11, 2005; Provisional Patent Application No. 60/698,941, filed Jul. 14, 2005; Non-provisional patent application Ser. No. 11/267,321, filed Nov. 7, 2005; Non-provisional patent application Ser. No. 11/267,266, filed Nov. 7, 2005; and Provisional Patent Application No. 60/748,148, filed Dec. 8, 2005, which are each are hereby incorporated by reference.

BACKGROUND OF THE INVENTION

1. Field of the Invention

This invention relates in general to an endoluminal surgical procedure for the treatment and control of obesity and, more particularly, to gastric rings and a novel method for the endoluminal implantation of the rings.

2. Discussion of the Related Art

Methods used in the prior art to treat obesity include gastric bypass and small bowel bypass surgery. Stapling of portions of the stomach has also been used to treat morbid obesity. This includes both vertical and horizontal stapling and other variations which will reduce the size of the stomach and make a small stoma opening. Many problems have been associated with the use of staples. First, staples are undependable. Second, staples may cause perforations in the stomach wall. Finally, the pouch or the stoma formed by the staples may become enlarged over time, thereby making the procedure useless.

A promising method for weight control employs the placement of a band around a portion of the stomach by open or laparoscopic surgery, thereby compressing the stomach and creating a stoma that is less than the normal interior diameter of the stomach. The constricted stoma restricts food intake into the lower digestive portion of the stomach. Such a band has been described by Kuzmak et al in U.S. Pat. Nos. 4,592,339, 5,074,868, and 5,226,429, which are hereby incorporated by reference.

These devices, known as gastric bands, require a surgical procedure for their implantation, which includes accessing the patient's stomach and other internal organs via incisions. The invasiveness related to these surgical procedures can cause pain, prolonged recovery, complications, and great expense to the patient and to the healthcare system. Moreover, the procedure can also be technically challenging for the surgeon.

Suturing devices described by Bjerken in U.S. Pat. No. 6,464,707 and in U.S. patent application Ser. No. 11/267,266 enable an operator to remotely place suture material within a closed space such a hollow body organ. Such devices enable the endoluminal implantation of prostheses, correction of defects, and the reconfiguration of tissue without the need for surgical incisions. U.S. Pat. No. 6,464,707 and U.S. patent application Ser. No. 11/267,266 are hereby incorporated by reference in their entirety.

SUMMARY OF THE INVENTION

The present invention includes prostheses, such as a ring, or series of rings; a suturing device; and a method for suturing prostheses within a subject. The rings are adapted to hold tissue in place around their circumference to create a constriction within an organ. If the organ is a stomach, the constriction is positioned such that a pouch of a certain volume is created proximal to the constriction, leaving a narrow passage to the remainder of the stomach's volume distal to the constriction. The suturing device is adapted to be passed into a patient's digestive system via a natural orifice, such as the mouth or anus. The suturing device can be adapted to expand once inside an organ and place multiple sutures in tissue around the circumference of the suturing device. After deploying suture, the device can be adapted to collapse to its original size to enable the withdrawal of the device. The rings are adapted to be held in place within an organ by the sutures.

BRIEF DESCRIPTION OF DRAWINGS

The invention may take form in certain components and structures, preferred embodiments of which are illustrated in the accompanying drawings.

FIG. 18 illustrates a view of a needle deployment at the proximal end of the suturing device.

FIG. 19 further illustrates another view of a needle deployment at the proximal end of the suturing device.

DETAILED DESCRIPTION OF INVENTION

The present invention is more particularly described in the following examples with reference to the accompanying drawings that are intended as illustrative only since numerous modifications and variations therein will be apparent to those skilled in the art.

Figure 1:
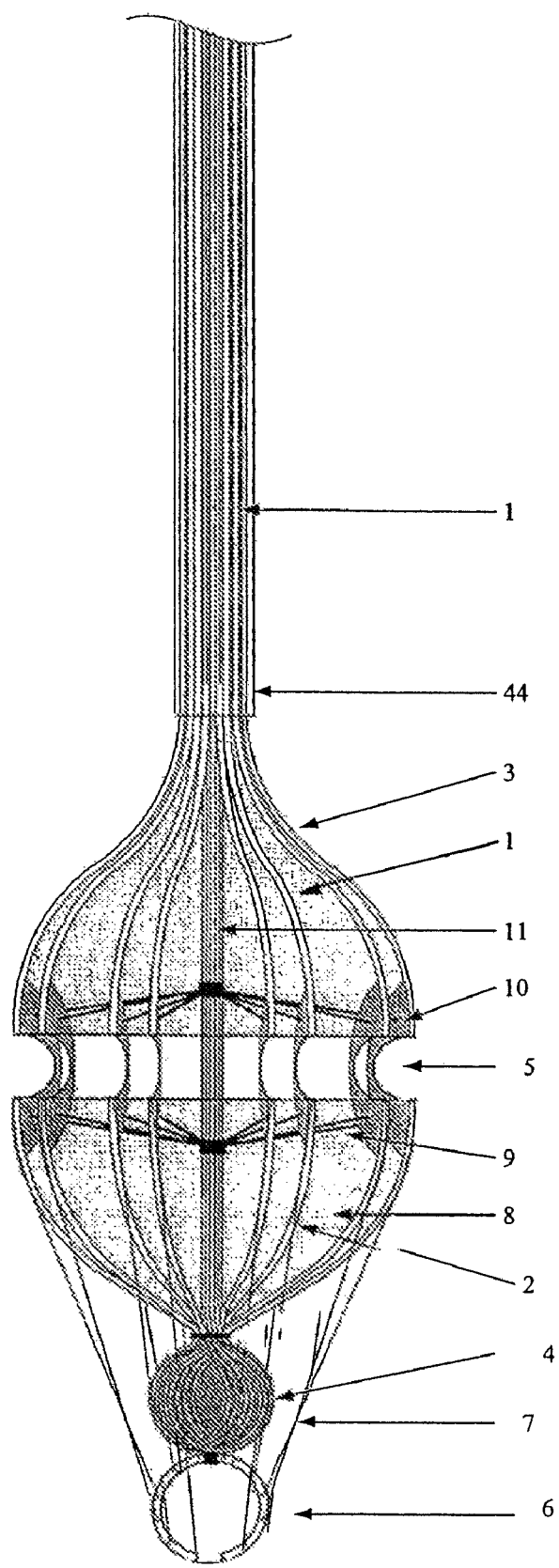
FIG. 1 illustrates a view of an exemplary embodiment of the present invention with the suture engagement area expanded.

For the placement of gastric rings or other implants within a patient shown in the exemplary embodiment of FIG. 1, the suturing device of the present invention may include an enclosure 1 and sheath 44. The enclosure 1 and sheath 44 have flexibility to help facilitate insertion, internal navigation, and positioning within a patient's body. The enclosure 1 and sheath 44 can be transparent, translucent, or opaque. The enclosure 1 and sheath 44 have a diameter and flexibility that is amenable for insertion into a natural body orifice, such as the mouth or anus, or into a surgical incision or existing stoma. The diameter of the sheath 44, which receives the enclosure 1, can be, for example, about 10 mm to about 22 mm for oral insertion and about 10 mm to about 35 mm for anal insertion. For other applications such as cardiac and vascular, the diameter can range from about 3 mm to about 35 mm in diameter.

In one embodiment, the enclosure 1 has a length sufficient to span the distance from its place of insertion to the targeted surgical location. For example, in gastrointestinal (GI) uses, the enclosure 1 can be approximately 2 to 3 feet. The length of the enclosure 1 for this embodiment should enable the device to reach several organs within the GI tract or within the abdominal cavity while a proximal end of the enclosure remains outside the patient's body and accessible to the operator.

The enclosure 1 and sheath 44 can be circular in its cross-section or it may have a non-circular cross-section. Possible cross-sectional shapes are oval, rectangular, or irregular, such as the shape of a mitral valve annulus.

The enclosure 1 and sheath 44 can house an endoscope (not shown). The device may include and be connected to the endoscope, or the endoscope may work in concert with the device. The device may also work without an endoscope.

Generally, an operator manipulates the enclosure 1 and sheath 44 to place the device at a desired location. The endoscope contained within the enclosure 1 and sheath 44 of the device may assist in directing the device to the desired location by applying force to the wall of the sheath 44, to steer the device. Alternatively, the enclosure 1 and sheath 44 may have the ability to direct or steer itself by using various methods of steering. For example, a balloon catheter (not shown) can run parallel within or along a side of the enclosure 1. A catheter (not shown) may be endoscopically placed in a defect, annulus, valve, or outlet, and inflated to hold the device in place. The sheath 44 can then be slid down the catheter (not shown) to be positioned and maintained in the desired location. In vascular applications, the device can be directed in a similar fashion following a guide wire (not shown). The enclosure 1 or sheath 44 can incorporate radio opaque markers (not shown) to enable visualization using fluoroscopy. In yet another embodiment, wires or cables can be used by varying tensions to turn the device within the closed organ or space. Steering the device may not be necessary for the implantation of gastric rings within the stomach.

Figure 2:
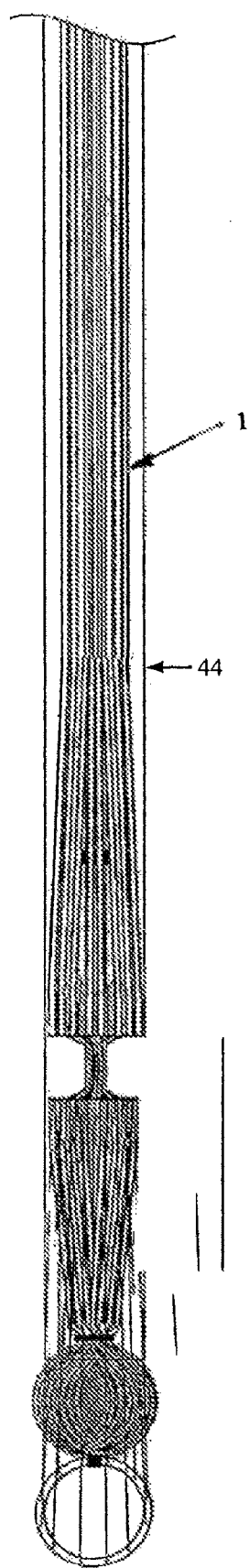
FIG. 2 illustrates a view of an exemplary embodiment of the present invention with the suture engagement area collapsed.
Figure 3:
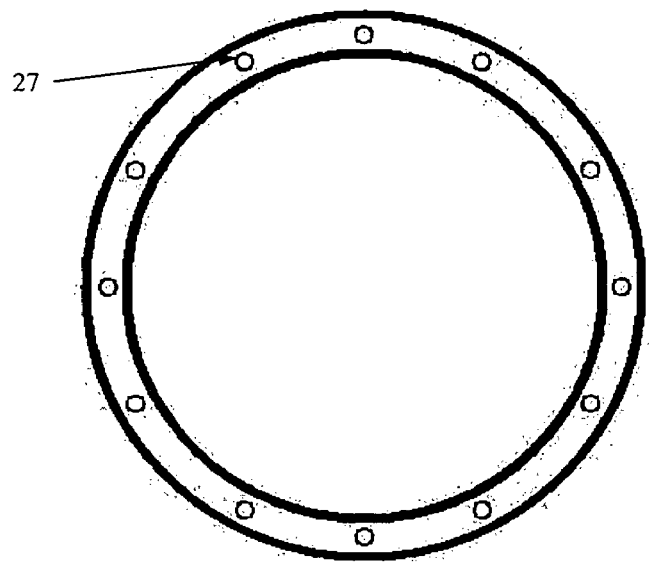
FIG. 3 illustrates a plan view of a gastric ring according to one embodiment of the present invention.
Figure 4:
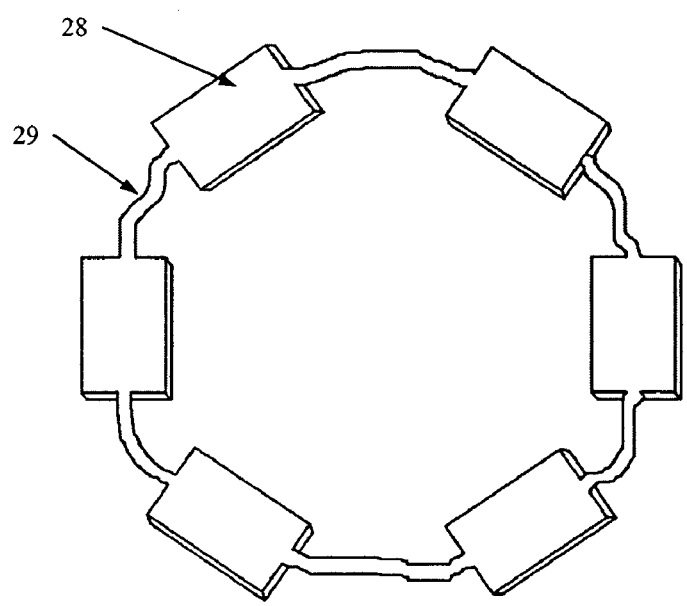
FIG. 4 illustrates a plan view of a gastric ring according to another embodiment of the present invention.
Figure 5:
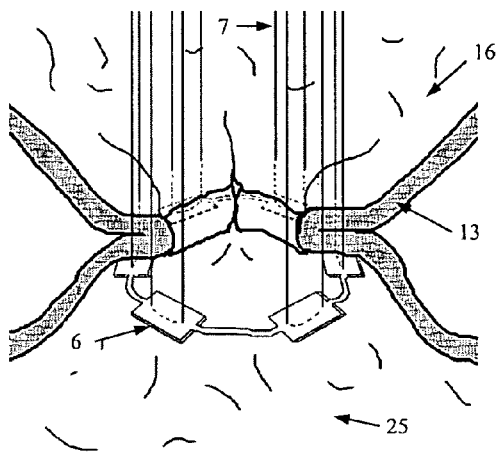
FIG. 5 illustrates a sectional view of a distal gastric ring being implanted.
Figure 6:
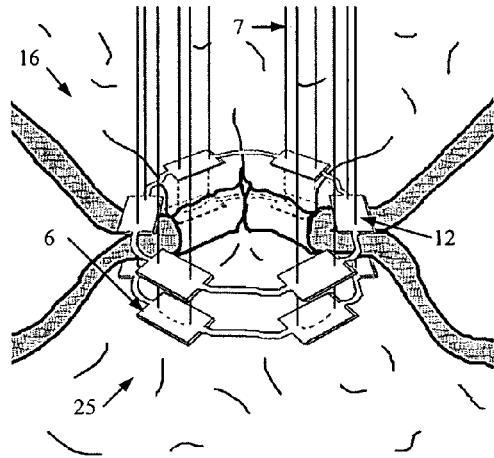
FIG. 6 illustrates a sectional view of distal and proximal gastric rings being implanted.

The enclosure 1 can be in fluid communication with a vacuum source and can include or define one or more suction ports 5. The port 5 is generally located near the distal end of the enclosure 1, although other locations are possible. The suction port 5 can completely or partially circumscribe a portion of the distal end of the enclosure 1. In one embodiment, the device has a series of suction ports spaced around its circumference. Generally, the area immediately distal and proximal to, and including, the suction port 5 is designed to expand and contract in diameter as shown in FIGS. 1 and 2, respectively, and described in further detail below. The suction port 5 can draw tissue into a bore of the enclosure 1 when a vacuum is applied to the enclosure 1.

One or more cannulas 2, 3 are arranged within the enclosure 1. In the illustrated embodiment, for example, in FIGS. 1 and 2, the cannulas include delivery cannulas 2 and corresponding receiving cannulas 3 arranged in series on opposite sides of the suction port 5.

Generally, a cannula is a tubular passageway though which material can travel in either a forward or backward direction. Each cannula has an internal diameter adequate to contain one or more needles and accompanying sutures.

Figure 25:
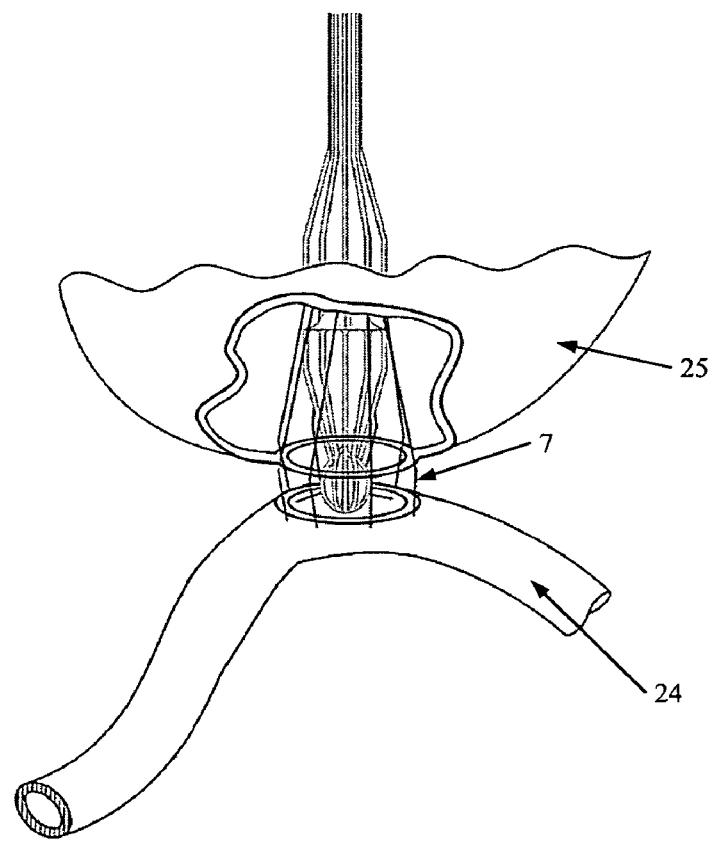
FIG. 25 illustrates a view of an exemplary embodiment of the suturing device of the present invention used for tissue to tissue anastomosis.
Figure 26:
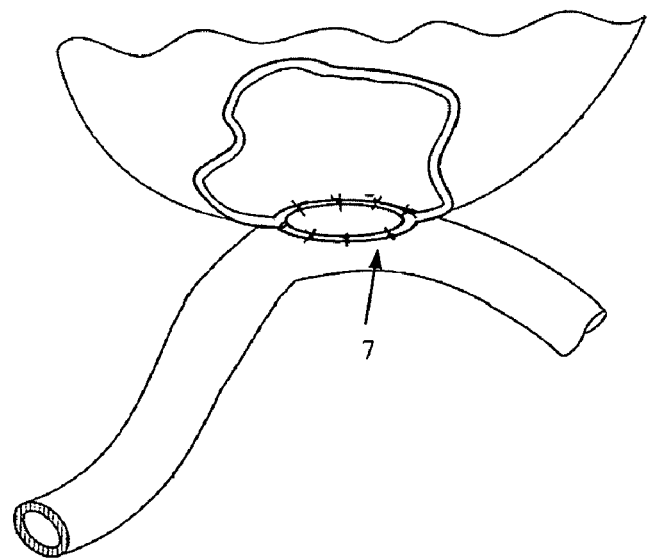
FIG. 26 illustrates a view of a tissue to tissue anastomosis resulting from the suturing device of FIG. 25.

The cannulas 2, 3 are utilized to direct needles 20 to an intended point of incorporation with tissue. The cannulas 2, 3 maintain the movement of the needles in a forward or backward direction and contain or prohibit lateral movement and bending of the needles. Although the cannulas 2, 3 are referred to as "delivery" and "receiving cannulas" herein, either set of cannulas can deliver or receive the needles. The delivery cannulas 2 loop at cannula loop 4 and extend up through the central portion of device via a central delivery cannula shaft 11. The central delivery cannula shaft 11 can be a single shaft through which the needles 20 extend, or a collection or bundle of individual cannulas. The receiving cannulas 3 can be bundled or formed together in a similar fashion proximal to the expandable area of the enclosure 1. The needles 20 can be manipulated via the portions of the needles extending out of the proximal end of the device, as shown in FIG. 18. The needles 20 proceed through the device via the delivery cannulas 2, cross the suction port 5, and extend back out of the device via the receiving cannulas 3, and out of the enclosure 1 and sheath 44, as shown in FIG. 19. The needles 20 leave the attached sutures 7 incorporated in the tissue. If the desired result is to attach two portions of tissue together to form an anastomosis, after the first portion of tissue has been penetrated by the needles, the needles can be reloaded by pushing them back into the delivery cannulas 2 after the device has been disengaged from the first portion of tissue. The device is then repositioned so that a second portion of tissue is drawn in to the suction opening and the needles penetrate the second portion to incorporate the sutures into the second portion of tissue. The sutures can then be secured, fastening the first portion to the second portion, as shown in FIGS. 25 and 26.

The cannulas 2, 3 can be formed, molded, and/or cast as part of the enclosure 1, or can be independent components inserted into the enclosure 1. The cannulas 2, 3 can be flexible, but may optionally have rigid sections as necessary to allow turning and targeting of the needles 20. The cannulas 2, 3 may be made of extruded plastic tubing reinforced with braided stainless wire.

The cannulas 2, 3 can be configured within the enclosure 1 in many ways. The cannulas 2, 3 may have flared or trumpet shaped openings (not shown) to assist in receiving the needles 20 once they have traversed the suction port 5.

The needles 20 completely traverse the tissue drawn within the suction port and may enter the receiving cannulas 3 at or near the upper side of the suction port 5. This creates a "bite" or suture of tissue.

The suturing device of the present invention generally utilizes long suture needles 20 made of a material that has the properties of shape memory, such as Nitinol. Nitinol is a nickel and titanium alloy that quickly returns to an original configuration after being flexed. Other materials can also be used, such as stainless steel. In one embodiment, the suture needles 20 can be of adequate length to reach a suturing site, via a natural body orifice such as the mouth or anus, or an incision or stoma, and return back out of the device. As such, the needles 20 are typically at least twice the length of the enclosure 1 of the device. As an example, a needle utilized for gastrointestinal applications can be approximately 6 feet long. The needles 20 can be attached to suture material to deliver and incorporate suture material 7 into tissue that the needles 20 traverse.

In one embodiment of the present invention, the needles are straight. The needles have a flexibility to follow the path within a cannula, 2, 3, which may include various turns and loops, without losing its original shape. The generally straight shape of the needles 20 allows them to exit the cannulas, 2, 3 transect a port or ports in the enclosure 1 such as a suction port 5, and proceed in the direction in which it has been directed.

The needles 20 can be longer or shorter depending on the desired application, such as cardiac, vascular, gynecological, proctological, pulmonary, and general surgical procedures, or depending on the embodiment of the present invention. The needles 20 may have a distal tip or end that is made of a material that is more rigid, such as steel or titanium. The needles 20 may have differing diameter or gauge depending upon the application. By way of example, vascular anastomosis generally requires relatively thin needles, for example, needles with a diameter of about 0.1 mm to about 0.5 mm. The needles 20 may also have an original configuration other than straight, such as having a bend, curve or coil.

In some embodiments, the suturing device does not use a vacuum source. The enclosure 1 may be of a size such that the tissue envelops or enters into a port 5 without the need of a vacuum. This embodiment can be useful, for example, in a tissue-to-tissue anastomosis or tissue defect closure application.

The circumferential suction port 5 illustrated in FIG. 1 may be used for incorporating sutures around an annulus or the circumference of a lumen or organ wall. The port 5 may be formed by two enclosure segments held together by one or more struts 10. The struts 10 hold the two segments defining the suction port at a predetermined distance. The struts 10 may have an inward curvature. As shown in FIG. 1, for example, concave suction port supports 10 can be provided. The curvature allows tissue to be drawn into the bore of the enclosure 1 about the entire circumference. When the expandable area of the device is in its collapsed configuration, the struts 10 can stack next to each other with members on either side of the central shaft 11.

Figure 23:
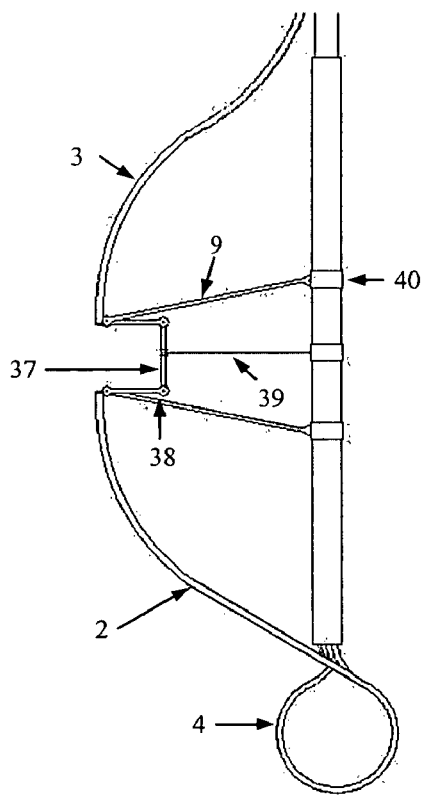
FIG. 23 illustrates a view of an expanded collapsible suction port strut utilized in an exemplary embodiment of the suturing device according to the present invention.
Figure 24:
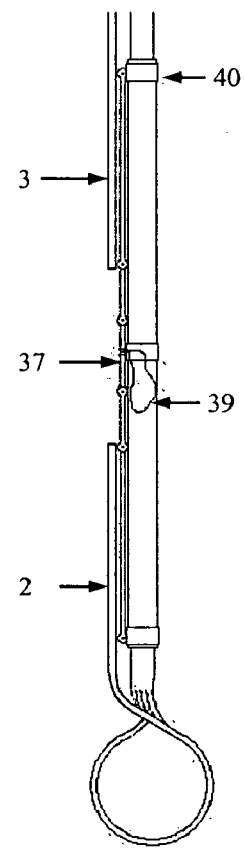
FIG. 24 further illustrates the exemplary embodiment of FIG. 23 in a collapsed state.

Alternatively, the curvature or inward concavity of the strut may be formed by two or more straight members with a hinge in the middle, so that when the hinge is pulled inward a V shape is formed. Also alternatively, as illustrated in FIGS. 23 and 24, straight members may form a rectangular shape. As shown in FIGS. 23 and 24, the hinged suction port strut embodiment allows for further reduction in the diameter of the device when in the collapsed configuration. In this embodiment, the suction port 5 is formed by the cannulas 2, 3 and strut members 37 connected with hinges 38. As shown in FIG. 24, in the collapsed state the strut members 37 and cannulas 2, 3 lay flat against the central shaft 11. To expand the device, sliding umbrella fulcrums 40 are slid together such that the umbrella struts are pushed outward. A flexible string or wire connection 39 of the hinged members 37 enables the members to deploy in the proper configuration by restricting the distance the member can extend from the central shaft 11.

The circumferential suction opening 5 for a circumferential placement of suture enables anastomosis, connection of tissue to tissue, or connection of tissue to a prosthetic graft. Particularly, the circumferential suction port enables the placement of a gastric ring or rings. In the embodiment shown in FIGS. 1 and 2, the device includes an enclosure 1 with a suction port 5 completely or partially circumscribing a portion of the distal end.

In another exemplary embodiment, a flexible plastic, non-porous fabric, or cellophane material 8 forms the expandable area of the enclosure 1. The distal end of the cannulas can be straight and made of a material such as metal or plastic. As shown in FIGS. 1 and 2, the distal end of the cannulas 2, 3 can be attached to the struts 9 that extend and retract, similar to the struts of an umbrella, when the fulcrum points 40 of their attachments are slid towards each other on a shaft 11. In this embodiment, when the struts 9 of the umbrella are extended, the flexible plastic, fabric, or cellophane material 8 makes up the wall of the enclosure 1 and forms the proximal and distal boundaries of the suction port 5. When the struts 9 are collapsed, the flexible plastic, fabric, or cellophane material 8 accordions down to size as demonstrated in FIG. 2. The diameter of the enclosure 1 near the suction port 5 may have the ability to expand in a range from approximately 10 mm to 150 mm. The struts 9 and fulcrum attachments 40 may be manipulated using a cable system. The thin sheath 44 may be slid up and down over the expandable area of the device in order to i) cover the open suction port and/or to ii) further compress the area facilitating insertion and withdrawal of the device from the patient.

In alternative embodiments of the suturing device, illustrated in FIGS. 20, 20A, 20B, 21, and 21A, the device eliminates the use of the relatively long needles 20, as well as the relatively long delivery cannulas 2 and the accompanying cannula loop 4 at the distal end of the suturing device.

Figure 20:
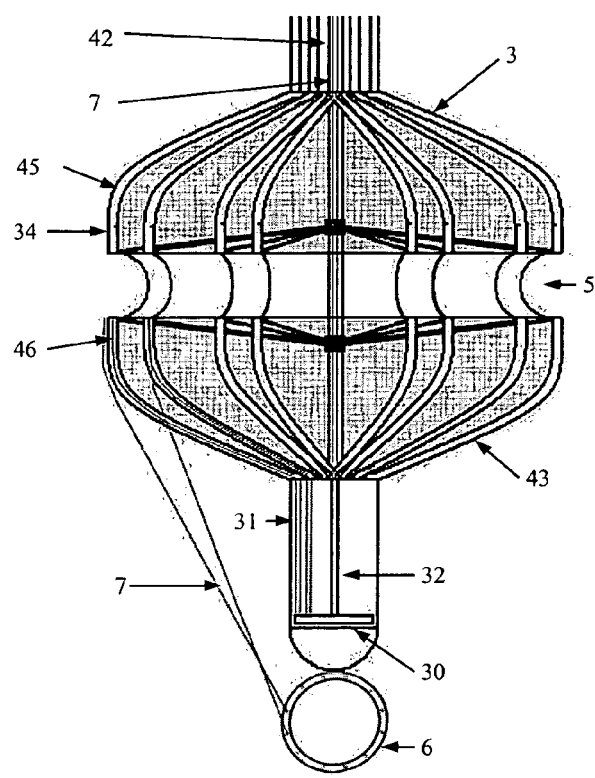
FIG. 20 illustrates a view of alternate exemplary embodiment of the suturing device according to the present invention.
Figure 20A:
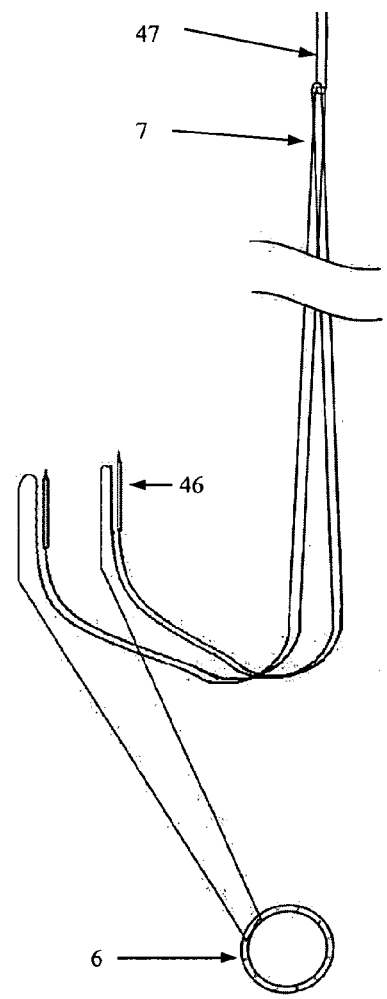
FIG. 20A illustrates a view of a suture configuration for an exemplary embodiment of the suturing device according to the present invention.
Figure 21:
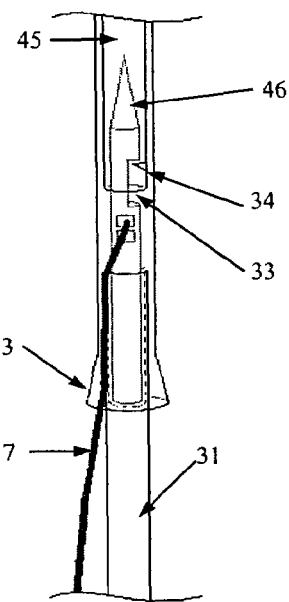
FIG. 21 illustrates a view of a needle catch system that can be utilized in the suturing configuration shown in FIG. 20A.

In the embodiment shown in FIGS. 20, 20A, and 21, relatively short pushrods 31 releasably hold a detachable needle tip 46 with attached suture 7. The pushrods 31 may be 3 to 6 inches long in the GI embodiment. The needle tip 46 has a recessed area or barb 33 near its sharpened point. The recessed area 33 on the needle tip 46 is adapted to receive a needle catch 34 within a receiving needle grasping rod 45. The distal ends of the pushrods 31 are mounted or held on a carriage or carousal 30 contained in the distal end of the enclosure 1. The carriage 31 is connected to a central shaft 32 that has the ability to lift the carriage 31 when actuated upward. The pushrods 31 are made of a flexible material, such as nitinol, that maintains its column strength when pushed in a forward or backward direction. The pushrods 31 extend upward and are directed through relatively short cannula segments 43 spaced around the circumference of the expandable region of the device. Generally, the cannula segments 43 do not extend down to the distal end of the enclosure 1. This allows the carriage 30 to move freely upward and downward within the distal portion of the enclosure 1. The distance between the carriage 30 in its most distal position and the distal end of the relatively short cannula segments 43 is the distance the pushrods 31 are able to be actuated up and down. The expandable area of the device at the suction port 5 has the ability to expand and contract as described above. In use, when the carriage 30 is actuated upward, the pushrods 31 will pass the detachably held needle tips 46 with an attached suture 7 across the suction opening 5. The needle tips 46 will enter the distal end of the receiving cannulas 3 and be engaged by the needle grasping receiving rods 45 contained therein. The needle grasping receiving rods 45 are then pulled upward within the receiving cannulas 3 contained within the enclosure 1. The configuration of the double-armed suture illustrated in FIG. 20A loaded into the device of FIG. 20 is described as follows: The needle tips 46 are passed through the material of the distal ring or prosthesis 6. The ring or prosthesis 6 is slid down the suture to the approximate midpoint. Each length of suture and the attached suture needle extending from the ring or prosthesis 6 can be described as a suture arm. The needle tips 46 are then backed into the relatively short cannula segments 43 in the device. The suture loop 7 extending from the back end of the needle tip and the ring or prosthesis is pulled through the relatively short cannula segment 43 for each needle 46. These suture loops 7 are gathered and maintained by looping a string 47 or similar length of material through the suture loops 7, and then this string is pulled up a central hollow shaft 42 running up the length of the enclosure 1. The string 47 maintains tension on the suture loops 7, enabling their management throughout the deployment of the needles 46 during the procedure. Releasing one end of the string 47 will release its hold on the suture loops 7.

Figure 20B:
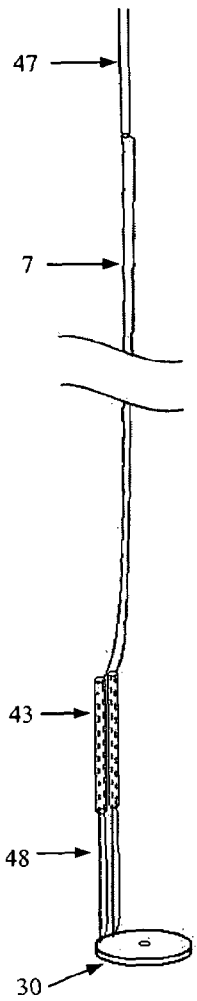
FIG. 20B illustrates a view of a suture configuration for another exemplary embodiment of the suturing device according to the present invention.
Figure 21A:
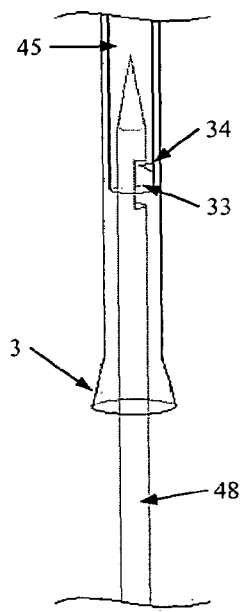
FIG. 21A illustrates an alternate view of a needle catch system that can be utilized in the suturing configuration shown in FIG. 20A.

In another embodiment illustrated in FIG. 20B, the detachably held needle tips 46 and the pushrods 31 are replaced with relatively short needles 48. The relatively short needles 48 are approximately 3 to 6 inches long. As illustrated in FIG. 20B, the needles 48 are backloaded through relatively short cannula sections 43 and releasably held by the movable carriage 30. As illustrated in FIG. 21A, the tip of the needle 48 has a recessed area or barb 33 near its sharpened point. The recessed area 33 on the needle tip 48 is adapted to receive a needle catch 34 within a receiving needle grasping rod 45. In use, when the relatively short needles 48 are raised within the enclosure 1 by the carriage 30, the needles 48 are directed by the relatively short cannula sections 43 so that the needles 48 traverse the suction port 5 and then enter into the receiving cannulas 3 to be engaged by the receiving needle grasping rod 45 and subsequently pulled up and through the length of the enclosure 1.

In each of the embodiments, the distal ends of the delivery cannulas 2, or alternatively, the relatively short cannula segments 43, may be spaced around the circumference of the suction port 5 in a variety of fashions. In an exemplary embodiment, the delivery cannulas 2 are spaced about the circumference of the suction port 5 such that they are spaced as pairs of cannulas. Each pair of cannula can contain the two suture needles 20, 46, 48 connected by the one suture length 7. The pair can be spaced approximately 1 cm apart from one another at their distal ends when the expandable area of the device is fully expanded. If the double-armed suture is back-loaded into each cannula pair, the loop of suture that bridges the two cannulas is incorporated with the intended distal prosthesis as described later.

The shape of the expandable area of the suturing device may be capsule, spherical, or football shaped with the cannulas 2, 3 distributed equidistant from the central shaft 11. Alternatively, the expandable area of the enclosure 1 may have an irregular shape that can be adapted to conform to the natural shape of the interior of the organ. The suction opening 5 may also be irregular or non-circular in circumference. The proximal section of the expandable area may have the approximate same surface area of interior of the created proximal organ pouch. In other words, the device can be useful to template the resulting gastric pouch.

FIGS. 5-11 illustrate the implantation of the ring 6 or rings 6, 12 and the creation of a gastric pouch 16. The size of the gastric pouch 16 may vary in size. Surgeons often cite 15 cc to 50 cc to be the target volume size of the pouch. The size of an outlet 14 created by the rings 6, 12 may also vary in size. Surgeons often cite a 10 mm to 15 mm diameter as the target size for the outlet 14.

The implantable gastric rings 6, 12 are used to hold or secure portions of the stomach wall around their circumference. Ring 6 is shown in FIG. 1. In one embodiment, two rings 6, 12 are used to create a restricted outlet 14 within an organ. In another embodiment, only one ring 6 is used and the suture loop on the opposite side of the tissue can be bolstered through the use of individual pledgets. The rings 6, 12 can serve as anchors for each other and for the sutures 7, which have been incorporated into the tissue wall 13, for example, as shown in FIGS. 5-8.

Figure 7:
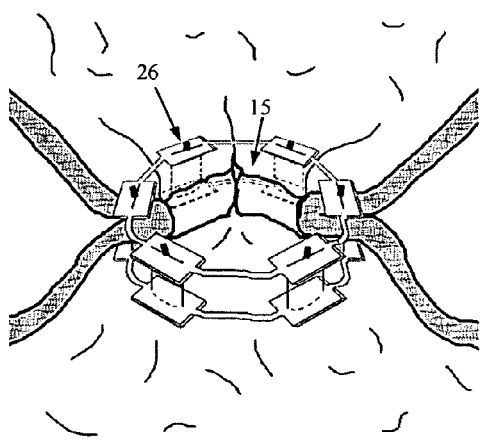
FIG. 7 illustrates a sectional view of the distal and proximal gastric rings implanted with sutures secured using endoscopic suture ties.
Figure 8:
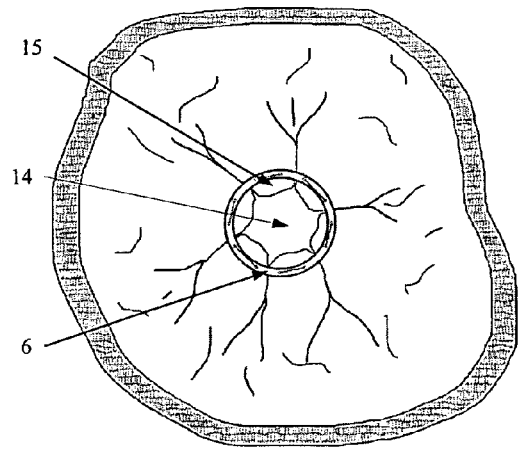
FIG. 8 illustrates a bottom cross-sectional view of the distal stomach pouch and the position of the distal gastric ring.

In the exemplary embodiment where two gastric rings 6,12 are employed, once implanted, the result is two rings 6, 12 held together with tissue sandwiched between them, as illustrated in FIG. 7. In the stomach, because the diameter of the organ's lumen can be substantially larger that the diameter of the gastric rings, the entire circumference of the organ may not be incorporated between the rings. Folds 15 from sections of the organ's circumference are held by the rings, similar to the configuration of a cinched sac or purse-string, as shown in FIG. 8. The pliability of the tissue folds can serve to create a competent or near competent proximal gastric pouch 16.

The tissue 15 held between the rings may protrude within the circumference of the rings, 6 12. This produces a small outlet 14 made up of the tissue 15 of the organ. The size of the resulting outlet 14 can be measured and altered as necessary for the particular patient at the time of implantation by varying the amount of tension between the rings and or by selecting a larger or smaller proximal gastric ring 12.

The rings 6, 12 are configured in a generally circular shape, although other configurations are possible, for example, an oval shape. The ring 6, 12 may contain holes or slots 27 through which suture can be passed. In another embodiment, the ring initially has no holes and the suture needles pierce the ring material 28 and are passed through. The rings 6, 12 can be made of a flexible material that can be temporarily held in any shape. Flexible rings 6, 12 can be made of biocompatible material such as plastic, silicone, polypropylene, Nitinol, stainless steel cable, Gortex, Nylon, Teflon, fabric, rubber, composites of material, or another like material that bends but does not necessarily stretch or have elastic properties.

Figure 17:
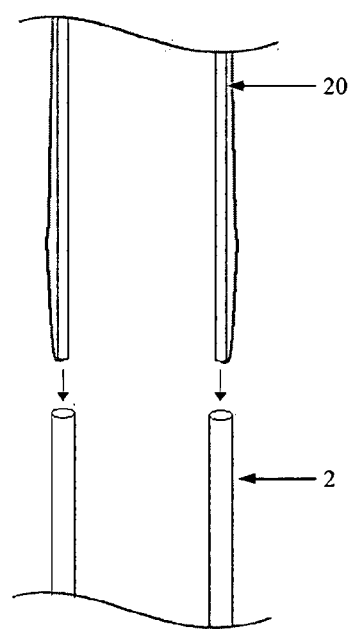
FIG. 17 illustrates a view of a double-armed suture with an incorporated distal gastric ring in the process of being back-loaded into a set of delivery cannulas.

The suturing device can be loaded with the double-armed sutures and the distal gastric ring 6 in the following manner. As illustrated in FIG. 17, each of the two needles 20 of the double-armed suture are passed through adjacent holes or areas 27, 28 in the distal gastric ring 6. Alternatively, the ring 6 may not have holes and therefore the needles 20 are passed directly through the ring material. The ring 6 is slid down both needles 20 and onto the suture material 7 to approximately the midpoint of the suture 7. The back ends of the needles, i.e. the end which connects to the suture, are pushed down adjacent delivery cannulas 2 until the sharpened points of the needles 20 are level or near level with the distal end of the delivery cannulas 2. The attached suture 7 rides along next to the needles 20 within the cannulas 2. This loading configuration is repeated for each double-armed suture to be loaded within delivery cannula 2 sets spaced around the circumference of the enclosure 1. The distal gastric ring 6 is mounted on the distal end of the enclosure 1 with the suture loops 7 incorporated. The ring 6 may be held in place at the distal end of the device by the tension applied by the sutures, or alternatively, there may be a cavity to house the distal ring 6. If double-armed sutures are employed, there will be an even number of cannulas 2, needles 20, and areas of incorporation 27 on the prosthesis.

Figure 12:
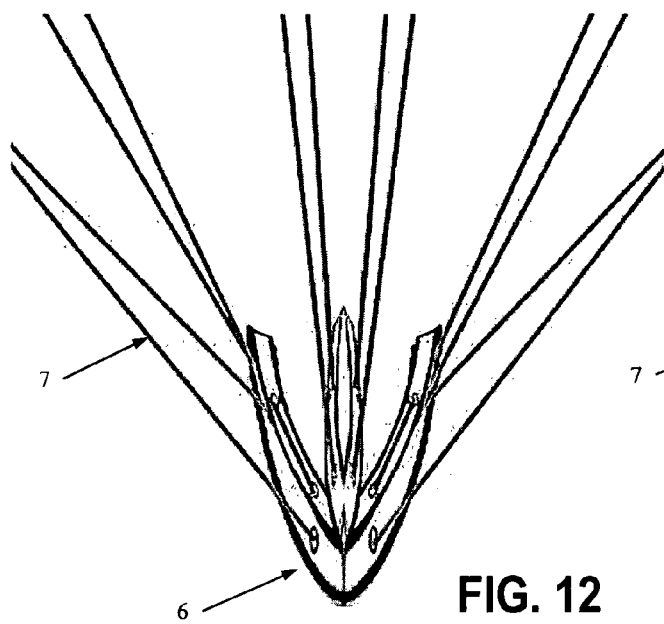
FIG. 12 illustrates a view of a circular gastric ring partially folded with incorporated sutures to facilitate insertion.
Figure 12A:
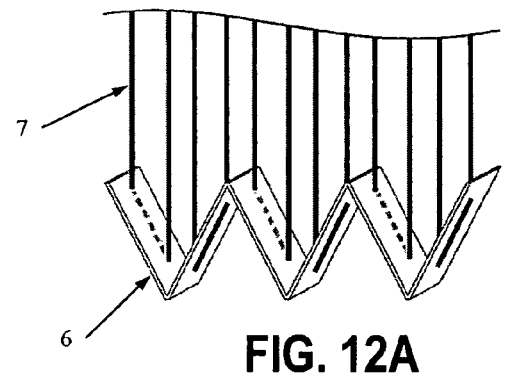
FIG. 12A illustrates a view of a straight gastric ring partially folded with incorporated sutures to facilitate insertion.
Figure 13:
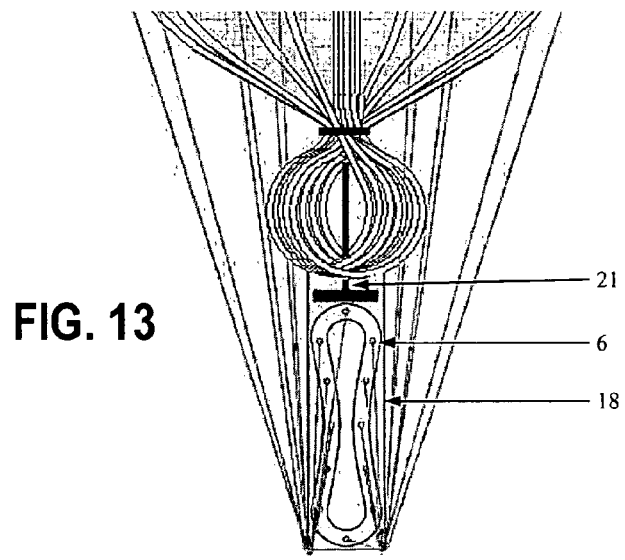
FIG. 13 illustrates a view of a flexible gastric ring releasably held on the distal end of the suturing device.

As illustrated in FIG. 13, the flexible ring 6 can be held in a narrow sheath, defining constraint 18, during insertion and then deployed once inside the targeted organ. The ring 6 can be folded as demonstrated in FIGS. 12 and 12A. Flexible gastric rings 6, 12 may range in diameter size from 10 mm to 150 mm. The flexible rings 6, 12 have the ability to bend and give as the natural muscular contractions of the stomach moves the organ. The ability of the rings 6, 12 to bend and give can help keep the sutures from tearing out of the tissue. The flexibility or flaccidness of the flexible rings 6, 12 also allow the created outlet 14 to close or collapse the opening, similar to the function of a natural sphincter, further restricting the food consumption capability of the patient and increasing the procedure's effectiveness.

Figure 14:
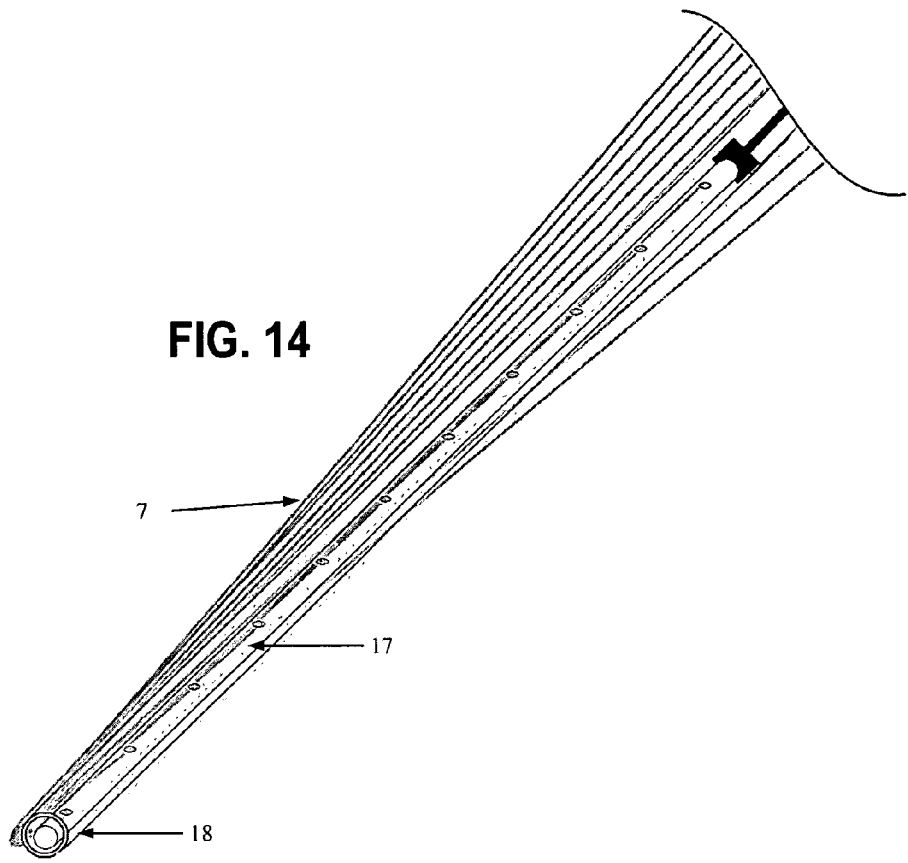
FIG. 14 illustrates a view of an embodiment of a gastric ring made of flexible or shape memory material that is temporarily held straight to facilitate insertion.

The flexible ring 6 may be a linear length of material that is implanted in a circular fashion, as illustrated in FIGS. 12A and 14-15A. The length of material can be incorporated with sutures and releasably held on the distal end of the suturing device, as shown in FIG. 14.

Figure 15:
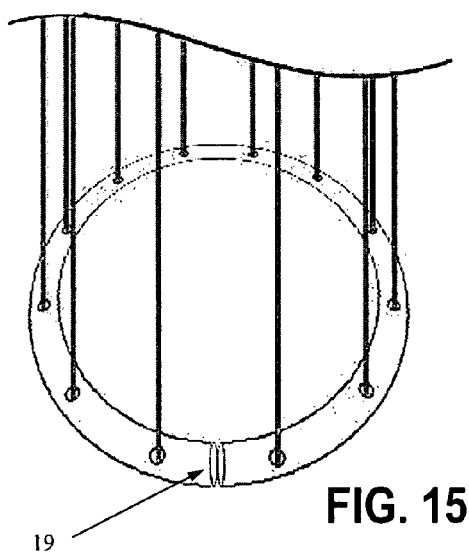
FIG. 15 illustrates a view of an embodiment of a gastric ring of FIG. 14 configured for implantation.
Figure 15A:
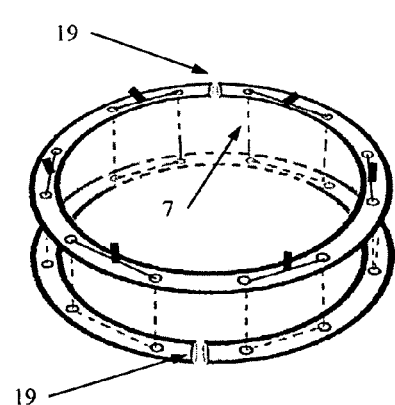
FIG. 15A illustrates a view of two gastric rings with breaks in their circumferences secured together such that their circumferential breaks are 180 degrees opposed to one another.
Figure 16:
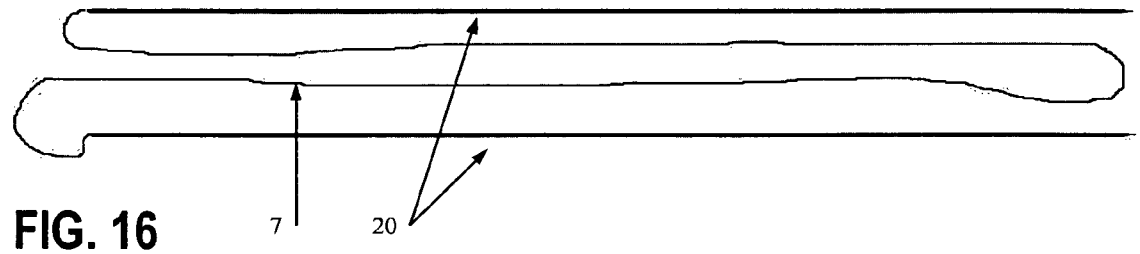
FIG. 16 illustrates a view of a double-armed suture used in the suturing device of the present invention.

In use, the suturing device deploys the incorporated sutures about the circumference of the lumen of an organ such as the stomach with unsecured mattress suture bites. A secured mattress suture bite can be provided wherein the two arms of a suture enter the first side of an object and/or tissue, exit a second side of an object and/or tissue and are secured together, forming a closed circuit of suture material. The flexible length of material is now held by the sutures distal to the tissue incorporated with the sutures. The second or proximal ring may now be incorporated with the sutures and lowered into the stomach and positioned above the length of material. The second proximal ring may be formed as a ring or it may be a length of material similar to the distal ring. If the proximal ring is a linear length of material, it can be incorporated with the sutures and aligned such that, when formed as a circle, the break in the circumference 19 formed by the two endpoints of the length of material are not be aligned with the break in the circumference of the distal ring. In an exemplary embodiment, the breaks 19 in the circumference should be 180 degrees apposed, as illustrated in FIG. 15A. The circumferential attachment of the two lengths of material with their endpoints misaligned produces a circumferential fixation that possesses hoop strength.

Rigid gastric rings with a diameter that is amenable to be passed trans-orally or trans-anally (10 mm-33 mm) can be formed as a closed circle. In another embodiment, as illustrated in FIGS. 12A, 14, 15 and 15A, the ring could be configured as an open circle having a length of material having two ends formed to make a circular shape. This material could be made of a material that has shape memory, such that the material could be formed in a round shape and then be held in a straight configuration, such as in a straight sheath, as illustrated in FIG. 14. When released from constraint 18 such as shown in FIG. 14, the material 17 would return to its round or predetermined formed shape. When utilizing two gastric rings with openings 19, the proximal ring should be incorporated with the sutures such that its opening 19 is 180 degrees opposed to the opening 19 on the distal ring. The opposition of openings 19 will provide the ring 6 with hoop strength to maintain circumferential fixation of the gastric tissue.

The rings 6, 12 can have any cross-section, for example, flat, round, oval, or irregular. The rings 6, 12 can have a diameter of 10 mm to 50 mm for gastric reduction, but rings can also have a diameter from 3 mm to 150 mm.

Closed rigid rings 6, 12 could be made of plastic, stainless steel, Nitinol, titanium, carbon fiber, or another like material which is compatible with biologic tissue.

The suture can be made of any material, for example, a non-absorbable material such as polypropylene. The size of the diameter of the suture may vary, although a 3.0 or 2.0 size suture can be particularly useful. The length of the suture connecting the two suture needles needs to be of adequate length to span the length of the two suture needles, plus the slack needed to loop through the gastric ring or other prosthesis. For example, if the length of the needles 20 utilized is six feet, then the suture 7 connecting them would need to be approximately thirteen feet.

Figure 9:
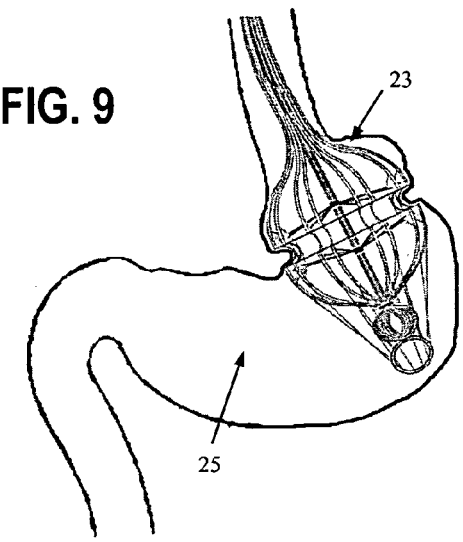
FIG. 9 illustrates a view of the suturing device expanded and drawing in tissue within the stomach.
Figure 10:
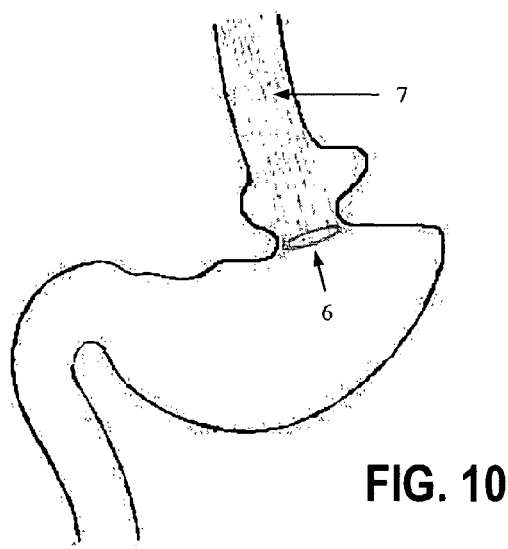
FIG. 10 illustrates a view of the distal gastric ring incorporated with a series of suture material running up and out of the patient's esophagus.
Figure 11:
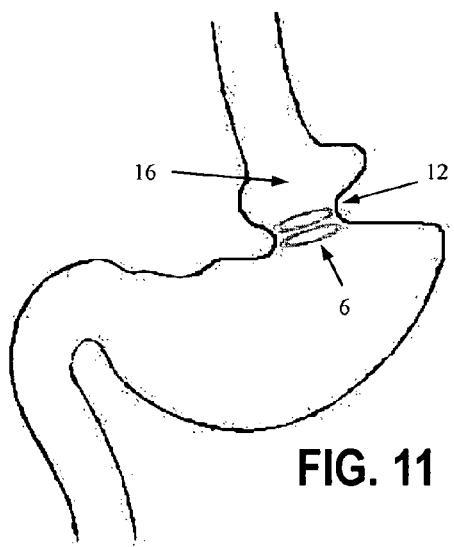
FIG. 11 illustrates a view of the distal and proximal gastric rings implanted within the stomach to create a proximal stomach pouch of a limited volume.
Figure 22:
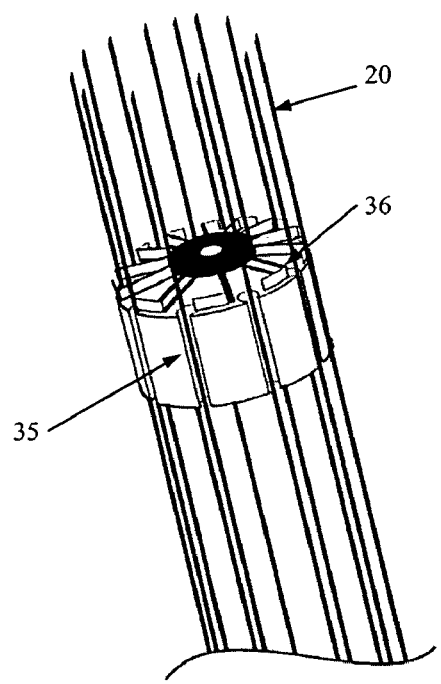
FIG. 22 illustrates a view of a suture needle organizer utilized in an exemplary embodiment of the suturing device according to the present invention.

To implant the gastric rings 6, 12, the device, loaded with the distal gastric ring 6, is inserted in its collapsed configuration, as shown in FIG. 2, through the patient's mouth. Once in the stomach, in this embodiment, the expandable portion of the enclosure 1 is expanded to increase the diameter of the suture engagement area which includes the suction port 5 circumscribing, or partially circumscribing the enclosure 1, as shown in FIG. 9. The enclosure 1 is pulled towards the patient's head so that the expandable portion is situated in the top of the stomach. The vacuum is applied, drawing tissue into the suction port 5. In this embodiment, the cannulas 2, 3 are back-loaded with suture needles as described above. As illustrated in FIG. 18, the long Nitinol needles 20, which are back-loaded into the delivery cannulas 2 and extend out of the proximal end of the delivery cannulas 2 and the enclosure 1 and sheath 44, such that the needles 20 can be manipulated by an operator, are manually, or mechanically, pushed by the operator through the delivery cannulas 2. The needles 20 cross the suction port 5, penetrate the drawn in tissue, and extend up into the receiving cannulas 3. As illustrated in FIG. 19, the needles 20 are grasped and pulled completely through and out of the device, leaving the sutures 7 extending through the tissue. The vacuum is deactivated and the expandable area 23 of the device is collapsed. The releasably held distal gastric ring which had been held in place on the device by the suture loops is released. The device is withdrawn from the patient. The suture 7, now incorporated and anchored in the stomach wall tissue, stays in place as the suture arms flow out of the receiving cannulas 3 via the suction port 5 as the device is withdrawn. The tension of the sutures 7 can be manipulated to position the gastric ring 6. In this embodiment, the pre-loaded distal gastric ring 6 is a distal gastric ring implant. As illustrated in FIG. 22, a suture/needle organizer can be employed to maintain the order of the needles as they are situated about a circumference. If a proximal gastric ring 12 is to be utilized, the needles 20 are passed through and incorporated into the proximal gastric ring 12. The operator uses an endoscope or other mechanism to push or slide the proximal gastric ring 12 down the patient's esophagus and into the stomach as tension is maintained on the sutures 7, such that the proximal gastric ring 12 slides down the sutures 7. The proximal gastric ring 12 is lowered into its position with the incorporated tissue folds separating it from the distal gastric ring 6. Proper tension is applied to the proximal gastric ring 12 and to the sutures 7, approximating the proximal gastric ring 12 over the distal gastric ring 6 with the incorporated tissue folds 15 between them. The sutures 7 are then secured by using suture anchors or by tying the sutures. The suture 7 arms are cut and withdrawn from the patient. The rings are now implanted, creating a small pouch 16 at the top of the stomach with a narrow outlet 14 leading into the distal stomach 25.

Because the implantation of the rings 6, 12 involves multiple needles 20 and attached suture 7 arms, the needles and suture arms should be maintained in their proper configuration or order throughout the implantation procedure. Procedures and devices may be used to maintain suture arm order. Clamps can be used to grasp each suture arm and then maintain the order of the clamps until the proximal prosthesis is incorporated. Alternatively, a mechanism that has the ability to releasably hold needles or suture arms about its circumference may be used, as illustrated in FIG. 22. Each needle or suture arm can be placed in a corresponding port or slit 35, while a mechanism 36 to releasably hold them in place is either opened or closed around the port or slit 35.

Figure 27:
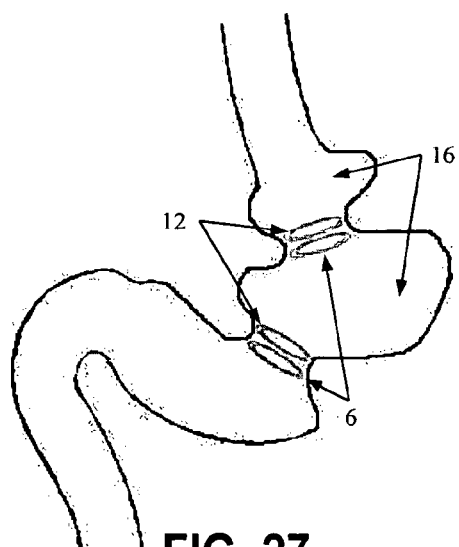
FIG. 27 illustrates a view of two sets of gastric rings implanted within the stomach.

As illustrated in FIG. 27, multiple sets of rings can be implanted within a single organ. Implanting additional sets of rings creates additional outlets 14 and additional organ pouches 16. Additional outlets and organ pouches may further restrict the capability of the patient to intake food and may slow the patient's gastric emptying time, thereby increasing the effectiveness of the procedure. In use, the implantation procedure of multiple sets of rings may be staged as follows; The first distal ring 6 of the first set of rings is a flexible length of material such as illustrated in FIGS. 12A, 14, and 15. Utilizing a first suturing device, the first distal ring 6 of the first set of rings is incorporated into the organ tissue with suture as described earlier. The first suturing device is withdrawn from the patient leaving the suture arms running up the esophagus and out of the mouth of the patient. The suture arms are maintained in an orderly fashion and set aside. A second or reloaded suturing device holding a second distal ring 6 of the second set of rings is subsequently introduced into the patient's organ and positioned such that the suction port 5 of the second suturing device is distal to the incorporation site of the first distal ring 6. The second distal ring 6 of the second set of rings may be configured as a length of material or as material formed as a circle with a closed circumference. The second distal ring 6 of the second set of rings is incorporated into the organ tissue with suture as described earlier. The second suturing device is withdrawn and the sutures from the second device are now incorporated with the second proximal ring 12. The second proximal ring 12 is positioned and secured to the second distal ring 6 as described earlier, creating a second or distal outlet 14. The suture arms from the first suturing device are now incorporated with the first proximal ring 12, positioned and secured to the first distal ring 6 as described earlier, creating a first or proximal outlet 14. The organ now has a proximal, intermediate, and distal pouch.

If necessary, the gastric ring implantation procedure can be easily reversed by simply cutting the sutures connecting the rings while using endoscopic instrumentation, and removing the rings.

The distal or proximal gastric ring can be replaced with an alternate prosthesis such as a valve, stent, or graft utilizing the present invention. One-way valves utilizing leaflets or floppy tubes can be used in the gastrointestinal tract to prevent backflow of contents such as with gastroesophageal reflux disease (GERD). Expandable stents can be utilized to maintain a level of patency within a lumen. The suturing device of the present invention enables a stent to be secured at a location within the lumen, thereby prohibiting migration or movement of the stent after its endoluminal placement. The suture loops, which pass through the prostheses, can incorporate material that secure themselves and eliminate the need for tying. Self-tying U-clips made of a shape memory material is one example.

In one embodiment, the gastric ring can be described as a series of pledgets 28 connected to one another by a length of material 29 in the form of a circle, providing hoop strength to the tissue folds drawn into its circumference. In one embodiment, the material making up the pledget portions of the ring may be made of a material with different properties from the material making up the remainder of the ring's circumference. The pledget 28 function of the ring maintains the ring-to-tissue-to-ring configuration and connection while it prevents or retards the suture from tearing through the tissue. The ring, or closed circuit, function of the ring holds and maintains the incorporated tissue in a circumferential fashion as illustrated in FIGS. 7, 8, 11 and 27.

In one embodiment, as an alternative to the expandable umbrella struts, the expandable area of the device could expand by means of an inflatable member such as a balloon or balloons. The balloon or balloons, when inflated, would force the cannula outward to a preset diameter. Flexible strings or wires connecting the concave suction port struts to the central shaft can enable a predetermined radius size of the expanded area.

As illustrated in FIGS. 25 and 26, the device is suited for connecting two tissue lumens together. As an example, the device could be passed, through an incision or defect in the stomach 25 and then proceed into an incision or defect in the bowel 24. The suction port 5 of the device is advanced past the incision and into the bowel lumen. The expandable region of the device could then be expanded to a degree such that when the device is pulled back or withdrawn from the bowel incision, the tissue making up the lumen of the incision envelopes into the circumferential suction opening 5. The device is pulled further, now maintaining the tissue lumen in the concavity of the suction opening, until the proximal portion of the expanded area completely enters the stomach 25. The lumen of the stomach incision or defect will now envelope into the concavity of the suction opening. Now that the two tissue lumens are enveloped into the suction opening, a vacuum may be a applied to draw the tissue in even further, if necessary. The long suture needles 20 are now advanced as described earlier. The expandable area of the device is collapsed and the device is withdrawn from the patient, leaving behind the sutures incorporated into the two tissues. The sutures are then secured as described earlier, establishing a stomach to intestine anastomosis, as shown in FIG. 26.

Figure 29:
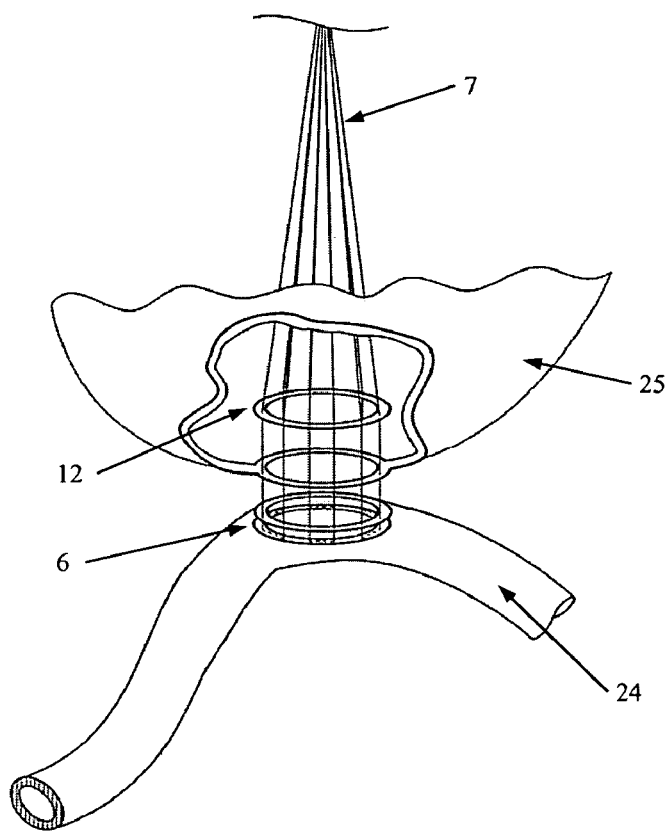
FIG. 29 illustrates a view an exemplary embodiment of the rings of the present invention used for tissue to tissue anastomosis.
Figure 30:
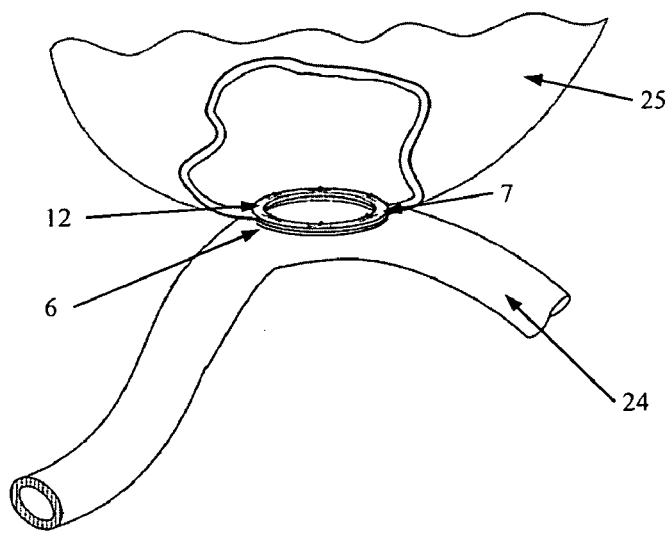
FIG. 30 illustrates a view of a tissue to tissue anastomosis resulting from the rings of FIG. 29.

As illustrated in FIGS. 29 and 30, the rings can be used to connect two tissue lumens. The suturing device can incorporate the first or distal ring 6 into the first tissue lumen around its circumference. The suturing device can be reloaded with the incorporated sutures 7 as described earlier. The suturing device can subsequently incorporate a second tissue lumen with sutures 7 around its circumference. The device can be withdrawn leaving sutures 7 incorporated with the first or distal ring 6, the first tissue lumen, and the second tissue lumen. The second or proximal ring 12 is incorporated with the sutures, lowered into position proximal to the distal ring 6 and the tissue of the first and second tissue lumens. The suture is then secured, fixing the first or distal ring 6 to the second or proximal ring 12 with the tissue of the first and second tissue lumens held between them, thereby connecting the two lumens.

The expandable portions of the enclosure proximal and distal to the suction opening 5 may expand and collapse in concert with one another, or alternatively, they may expand and collapse independently from one another.

The suture 7 on the distal ring 6 may not loop through the material, but may in fact be connected to, or formed together with, the distal ring such that each suture arm connects to the ring directly.

Figure 28:
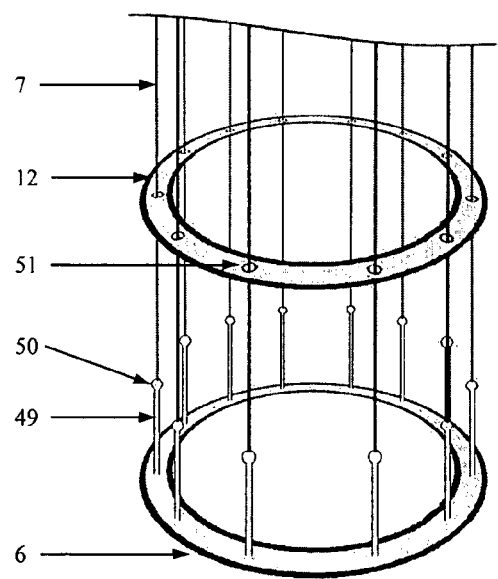
FIG. 28 illustrates a view of a set of self-fastening rings prior to their connection to one another.
Figure 28A:
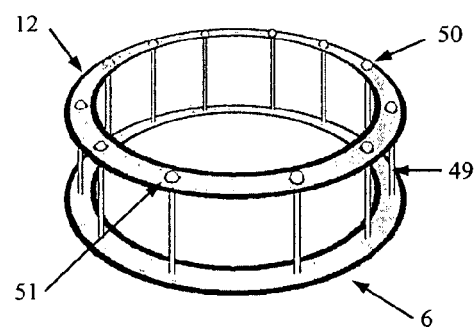
FIG. 28A illustrates a view of the set of self-fastening rings of FIG. 28 fastened to one another.

As illustrated in FIGS. 28 and 28A, the rings 6, 12 may be formed such that they can fasten together to eliminate the need to tie or otherwise secure sutures. Needles and sutures are connected to, or run through male connection members 49 of the distal ring 6, enabling the incorporation with tissue and remote incorporation with the proximal ring 12. The male connection members 49 of the distal ring 6 have distal anchors 50 that are of a size small enough to be pulled through the female connection slot 51 of the proximal ring 12, yet large enough as to not allow the member to easily return back through the female connection slot 51. In use, the distal ring 6 is incorporated with the tissue as described earlier. The proximal ring 12 is slide down the sutures 7 and positioned above the incorporated tissue and the distal ring 6. Tension on the sutures 7 will provide upward force on the distal ring 6, while endoscopic instrumentation applies downward force on the proximal ring 12. The male connection members 49 of the distal ring 6 extend through the incorporated tissue. The upward force on the distal ring 6 combined with the downward force on the proximal ring 12 enables the male connection members 49 to snap through the female connection slots, thereby fastening the distal ring 6 to the proximal ring 12 with the tissue folds fixated between them. The sutures 7 are now cut using endoscopic instrumentation.

The ring material of the rings 6 and 12 may be made of, contain, or coated with a biodegradable substance, such as a drug, that eludes a steady dose of the drug over time. This substance could be an appetite suppressant, a proton pump inhibitor, an anti-inflammatory drug, or other medication. For example, the drug can be an appetite suppressant that is eluded for a discrete amount of time to assist a patient in assimilating to their new eating pattern.

Plastic, rubber or cellophane sheaths may be used to cover the proximal ends of the needles 20 and attached sutures 7 prior to their deployment. The sheaths help maintain sterility of the needles 20 and suture 7 and will reduce the possibility of the suture loops 7 from becoming entangled with each other prior to, and as the needles 20 are being deployed.

Although FIGS. 18 and 19 illustrate a manual manipulation of the needles, the needles can also be mechanically manipulated. The cannulas and/or needles can include a code or color for identification.

What is claimed is:

1. A suturing device for suturing within a subject, comprising:
   a sheath having a length greater than a width thereof;
   an enclosure having a length that is greater than a width thereof, the enclosure slidably positioned within the sheath, wherein at least a portion of the length of the enclosure has a diameter adapted to expand when not positioned within the sheath, and the expandable diameter is maintained in an unexpanded state when the expandable portion is positioned within the sheath;
   at least one suction port comprising an opening circumferentially disposed in a sidewall of the enclosure, wherein the opening:
      has a length substantially less than the length of the enclosure, and
      is located on the expandable portion of the enclosure, wherein the suction port receives tissue within the enclosure to be sutured;
   at least one cannula arranged at least partially within the enclosure;
   at least one suture needle arranged within the at least one cannula and having a length at least twice as long as the length of the enclosure, wherein the needles are adapted to be pushed through the cannula and directed through the tissue received within the enclosure to provide a suture to the tissue.

2. The suturing device of claim 1, further comprising a prosthesis incorporated with the suture outside of the enclosure at the distal end of the device.

3. The suturing device of claim 1, wherein the enclosure is a tube.

4. The suturing device of claim 3, wherein the tube is flexible.

5. The suturing device of claim 3, wherein the tube is rigid.

6. The suturing device of claim 3, wherein the tube has a diameter and flexibility for insertion into an opening, and wherein the opening is at least one of a natural body orifice, a surgical incision, and an existing stoma.

7. The suturing device of claim 1, wherein the at least one cannula directs the at least one needle to the tissue to be sutured within the enclosure.

8. The suturing device of claim 1, wherein the at least one cannula substantially prevents lateral movement of the at least one needle.

9. The suturing device of claim 3, wherein the at least one cannula is formed as part of the tube.

10. The suturing device of claim 1, wherein the at least one cannula is made of extruded plastic tubing reinforced with braided stainless wire.

11. The suturing device of claim 1, wherein the at least one cannula comprises at least one delivery cannula that extends from a portion of the suturing device that remains outside of the subject during suturing to approximately the at least one suction port.

12. The suturing device of claim 11, wherein the at least one cannula further comprises at least one receiving cannula that extends from the at least one suction port to the portion of the suturing device that remains outside of the subject during suturing.

13. The suturing device of claim 12, wherein the at least one delivery cannula and the at least one receiving cannula cooperate such that the at least one needle is passed from the at least one delivery cannula, across the at least one suction port and through the tissue to be sutured, and into the at least one receiving cannula.

14. The suturing device of claim 11, wherein the at least one delivery cannula includes a bend at the distal end of the device.

15. The suturing device of claim 1, wherein the enclosure has a circular cross section.

16. The suturing device of claim 1, wherein the enclosure has a non-circular cross section.

17. The suturing device of claim 1, further comprising an endoscope for viewing the suturing.

18. The suturing device of claim 6, wherein the tube has a rigidity sufficient to enable manipulation at the opening.

19. The suturing device of claim 1, wherein the at least one cannula imparts a force upon to expand the diameter of the enclosure.

20. The suturing device of claim 1, further comprising a central shaft arranged within the enclosure, a sliding member arranged on the central shaft, and a strut attached to the at least one cannula at one end and to the sliding member positioned on the central shaft at the other end,
wherein sliding the sliding member up and down increases and decreases the distance of the at least one cannula from the central shaft.

21. The suturing device of claim 1, further comprising an inflatable balloon to control the expansion of the diameter.

22. The suturing device of claim 1, further comprising a flexible membrane forming at least a portion of the tube above and below the at least one suction port.

23. The suturing device of claim 1, wherein the portion of the enclosure is capsule, sphere, or irregular shaped.

24. The suturing device of claim 1, wherein the at least one suction port is adapted to be in fluid connection with a vacuum source such that, when a vacuum is applied, tissue is drawn into the at least one suction port and at least partially into the enclosure.

25. The suturing device of claim 24, further comprising a vacuum hose for connecting the enclosure to the vacuum source.

26. The suturing device of claim 1, wherein the at least one suction port completely circumscribes the enclosure.

27. The suturing device of claim 1, wherein the at least one suction port partially circumscribes the enclosure.

28. The suturing device of claim 1, wherein the at least one needle comprises a material with shape memory.

29. The suturing device of claim 1, wherein the at least one needle consists of a material with shape memory.

30. The suturing device of claim 1, wherein the at least one needle comprises a nickel and titanium alloy.

31. The suturing device of claim 1, wherein the at least one cannula includes at least two cannula.

32. The suturing device of claim 1, wherein the suturing device is adapted for fastening a stent within a lumen.

33. The suturing device of claim 1, wherein the at least one needle includes two needles arranged within the at least one cannula.

34. The suturing device of claim 1, wherein the at least one cannula has at least one flared opening.

35. The suturing device of claim 1, further comprising a vacuum source.

36. The suturing device of claim 1, wherein the device is sized to suture within a vessel.

37. The suturing device of claim 1, wherein the device is sized to suture within an organ or body cavity.

38. The suturing device of claim 1, wherein the at least one needle is adapted to be manipulated from outside the subject.

39. The suturing device of claim 1, wherein the suturing device is adapted for forming at least one of simple interrupted suture bites for connecting tissue.

40. The suturing device of claim 1, wherein the suturing device is adapted for forming simple interrupted suture bites for plicating tissue.

41. The suturing device of claim 1, wherein the suturing device is adapted for closing incisions or defects.

42. The suturing device of claim 1, wherein the suturing device is adapted for connecting one lumenal tissue to a second lumenal tissue or orifice.

43. The suturing device of claim 1, wherein the suturing device is adapted for connecting tissue to a prosthetic graft.

44. The suturing device of claim 1, further comprising a sleeve arranged on the exterior of the enclosure for selectively covering the at least one suction port.

45. The suturing device of claim 1, wherein the suturing device is adapted to narrow a diameter of at least one portion of an organ and a vessel by plication.

46. The suturing device of claim 1, further comprising an inflatable balloon catheter.

47. The suturing device of claim 1, wherein the enclosure has an unexpanded diameter of about 5 mm to about 22 mm.

48. The suturing device of claim 1, wherein the enclosure has an unexpanded diameter of about 3 mm to about 32 mm.

49. The suturing device of claim 1, wherein the device is adapted to effectively reduce the volume of an organ.

50. The suturing device of claim 1, wherein the suturing results in a gastric pouch.

51. The suturing device of claim 1, wherein the suturing results in an augmented gastro-esophageal junction.

52. The suturing device of claim 1, wherein the suturing results in reducing the diameter of an outlet or lumen.

53. The suturing device of claim 1, wherein the suture includes a suture anchor.

54. The suturing device of claim 1, wherein the at least one cannula includes at least one of a code and or color for identification.

55. The suturing device of claim 1, wherein the at least one suture needle includes at least one of code and color for identification.

56. The suturing device of claim 1, wherein the at least one cannula can direct the at least one needle in one direction, have the at least one needle exit the at least one cannula, be turned around, and directed back into the at least one cannula in the opposite direction.

57. The suturing device of claim 1, wherein the at least one cannula can direct the at least one needle in one direction, have the at least one needle exit the at least one cannula, then be backed back into the at least one cannula.

58. The suturing device of claim 1, further comprising a prosthesis incorporated with the suture outside of the enclosure at the distal end of the device.

59. The suturing device of claim 1, wherein the at least one needle is flexible with a rigid distal segment.

60. The suturing device of claim 1, further comprising a first push rod arranged within the at least one cannula to engage the at least one needle to push the needle across the at least one suction port.

61. The suturing device of claim 60, wherein, once the first rod has pushed the at least one needle across the suction port, the first rod is adapted to disengage from the at least one needle, and wherein the device further comprises a second rod arranged within the at least one cannula to engage the at least one needle to pull the needle completely across the suction port and then be able to push the needle back across the at least one suction opening.

62. The suturing device of claim 61, wherein the at least one needle is sharpened on each end and attached to the suture at approximately a mid-point of the at least one needle.

63. The suturing device of claim 62, wherein the at least one needle has a non-circular cross section.

64. The suturing device of claim 60, wherein the at least one set of cannulas are aligned in a vertical fashion such that the at least one straight needle can be shuttled across a suction port.

65. The suturing device of claim 1, wherein the at least one needle has sharpened points and a barb.

66. The suturing device of claim 1, further comprising at least one pushrod arranged in the at least one cannula to push the at least one needle in a forward and backward direction.

67. The suturing device of claim 66, wherein the at least one pushrod is of sufficient length to travel from outside the subject to the suction opening.

* * * * *